(12) United States Patent
Chung et al.

(10) Patent No.: US 7,919,959 B2
(45) Date of Patent: Apr. 5, 2011

(54) SIGNAL READOUT CIRCUIT OF AMPEROMETRIC SENSOR

(75) Inventors: Wen-Yaw Chung, Taoyuan Hsien (TW); Shao-Chun Cheng, Taipei (TW); Chiung-Cheng Chuang, Taoyuan County (TW); Febus-Reidj Guinto Cruz, Chung Li (TW); Dorota Genowefa Pijanowska, Nieporet (PL)

(73) Assignee: Chung Yuan Christian University, Chung Li (TW)

( * ) Notice: Subject to any disclaimer, the term of this patent is extended or adjusted under 35 U.S.C. 154(b) by 0 days.

(21) Appl. No.: 12/628,827

(22) Filed: Dec. 1, 2009

(65) Prior Publication Data
US 2010/0308796 A1     Dec. 9, 2010

(30) Foreign Application Priority Data

Jun. 3, 2009   (TW) ............................... 98118421 A (51) Int. Cl.
*G01R 1/30*        (2006.01)

(52) U.S. Cl. ................................. 324/123 R; 324/76.11
(58) Field of Classification Search ........................ None
See application file for complete search history.

(56) References Cited

U.S. PATENT DOCUMENTS

| 6,906,524 B2 * | 6/2005 | Chung et al. .................. 324/464 |
| 7,663,357 B2 * | 2/2010 | Chung et al. ................. 324/71.1 |

* cited by examiner

*Primary Examiner* — Minh N Tang
(74) *Attorney, Agent, or Firm* — Tim Tingkang Xia; Morris, Manning & Martin, LLP (57) ABSTRACT

A signal readout circuit comprises a first amplifier, a second amplifier and first to fourth transistors. The signal readout circuit has a first electrode, a second electrode, and a third electrode. The signal readout circuit applied in a wide current-sensing range of amperometric chemical sensing. The readout circuit may be applied in electrochemical sensing such as glucose, so as to read out a current signal of an amperometric sensor. Through a design of low input impedance, sensing signals in a wide current range can be sensed in the readout circuit. Also, a current mirror structure is used to copy the input current to an output current, such that an output signal range of the output signals of the current circuit is not limited by a supplied voltage.

11 Claims, 8 Drawing Sheets

FIG.8

SIGNAL READOUT CIRCUIT OF AMPEROMETRIC SENSOR

CROSS-REFERENCE TO RELATED APPLICATIONS

This non-provisional application claims priority under 35 U.S.C. §119(a) on Patent Application No(s). 098118421 filed in Taiwan, R.O.C. on Jun. 3, 2009, the entire contents of which are hereby incorporated by reference.

BACKGROUND OF THE INVENTION

1. Field of Invention

The present invention relates to a signal readout circuit, and more particularly to a signal readout circuit applied in a wide current-sensing range of amperometric chemical sensing.

2. Related Art

The earliest amperometric signal readout circuit was proposed by Turne, Harrison, and Baltes in 1987, and its major architecture is a two-electrode potentiostat. As the two-electrode sensing mode has a problem of concentration polarization, a three-electrode potentiostat was developed. However, the conventional operational mode is to convert an output signal—current into a voltage signal, in which a voltage range is limited by a power supply.

Figure 1:
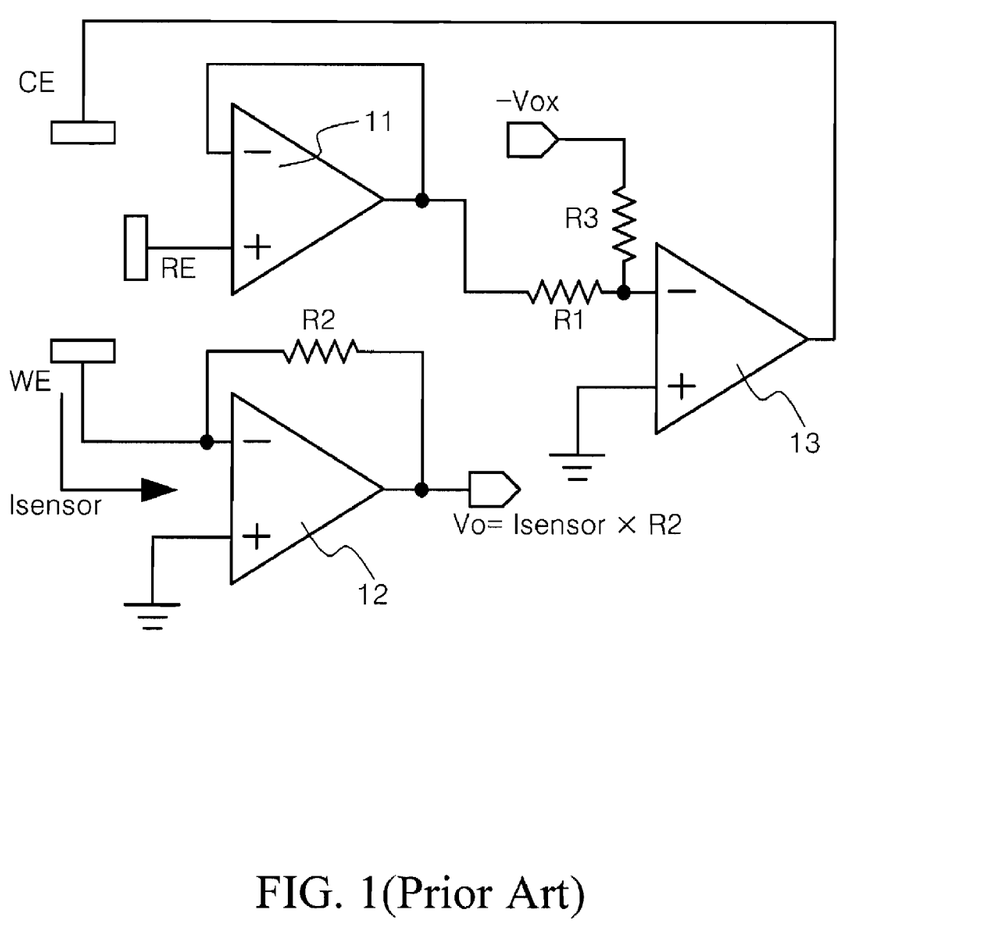
FIG. 1 is a schematic view of a typical three-electrode signal readout circuit.

FIG. 1 is a schematic view of a typical three-electrode signal readout circuit. The signal readout circuit is formed by a first amplifier 11, a second amplifier 12, and a third amplifier 13. A first input terminal of the first amplifier 11 is connected to a second electrode RE. A second input terminal of the first amplifier 11 is connected to an output terminal. A second input terminal of the second amplifier 12 is connected to the output terminal through a second resistor R2. The second input terminal is also connected to a first electrode WE. A first input terminal of the second amplifier 12 is connected to a ground terminal. An output terminal of the second amplifier 12 is an output terminal of a sensed signal. A first input terminal of the third amplifier 13 is connected to the ground terminal, and a second input terminal of the third amplifier 13 is connected to the output terminal of the first amplifier 11 through a first resistor R1, and another voltage −Vox is input to the second input terminal through a third resistor R3. An output terminal of the third amplifier 13 is connected to a third electrode CE. A sensing current Isensor is generated at the first electrode WE at first. An output voltage Vo of the output terminal of the third amplifier 13 is Isensor×R2.

The three-electrode signal readout circuit shown in FIG. 1 uses too many operational amplifiers (OPAs). In addition, the circuit needs dual power supply and has a problem of excessive power consumption. Therefore, in recent years, many improved circuits of potentiostats were proposed. However, these circuits have disadvantages such as excessive consumption, large chip areas, small sensing ranges, and nonadjustable measuring ranges, and the like.

Figure 2:
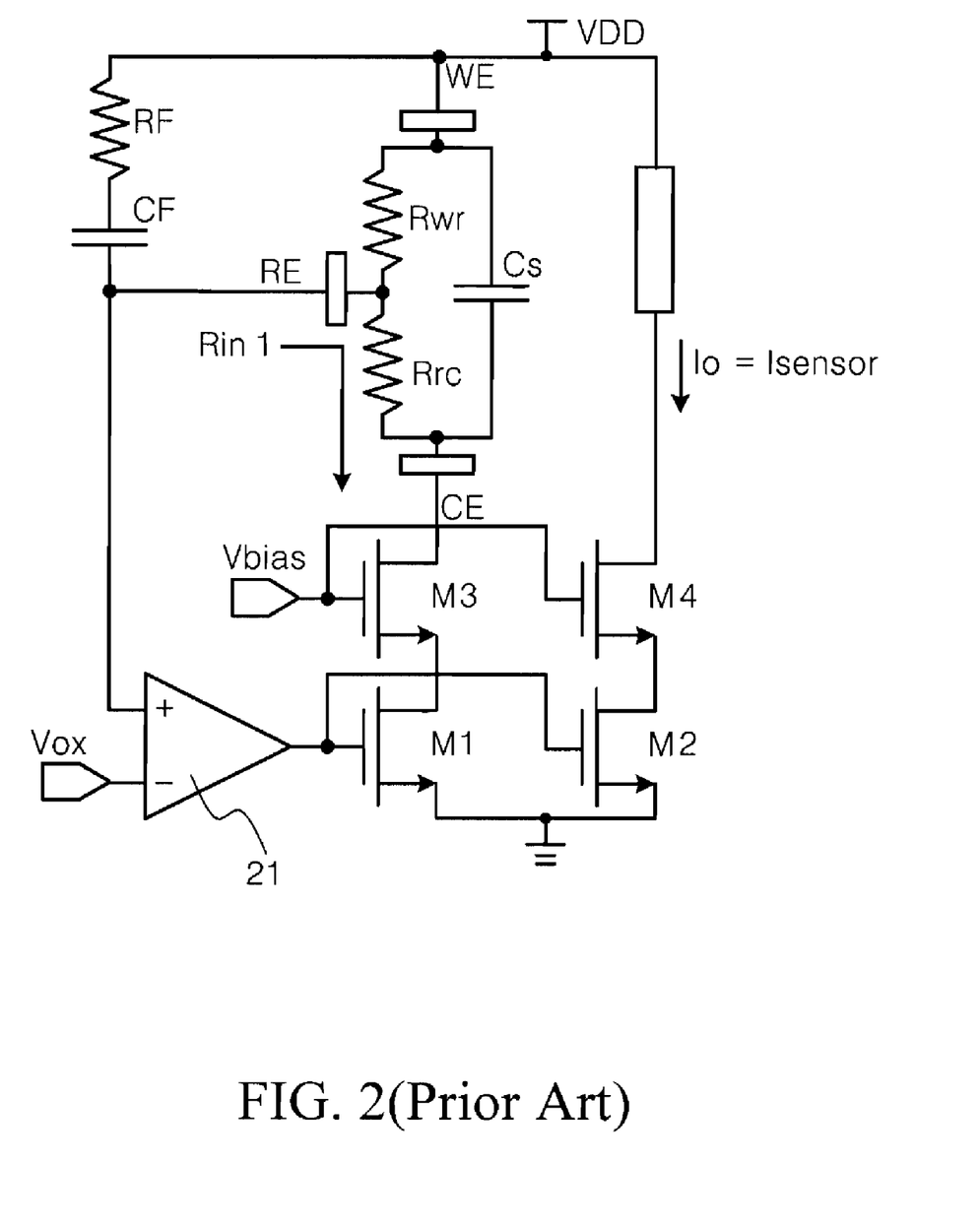
FIG. 2 is a schematic view of another typical three-electrode signal readout circuit.

FIG. 2 is a schematic view of another three-electrode signal readout circuit, in which a first amplifier 21, a first transistor M1, a second transistor M2, a third transistor M3, a fourth transistor M4, a first transistor M1, a second transistor M2, a third transistor M3, and a fourth transistor M4 form a cascode current mirror.

A resistor Rwr, a resistor Rrc, and a capacitor Cs are equivalent resistors and capacitor of a glucose solution. The resistor Rwr is a Faraday resistor, and a resistance of the resistor Rwr will decrease with the increase of the sensing current. The resistor Rrc is solution impedance. The capacitor Cs is an electric double layer capacitor of a working electrode. The resistor Rrc and the capacitor Cs will not change with currents. A resistor RF and a capacitor CF form a frequency compensation element of the circuit. A voltage Vox is an input pin for setting a potential of a second electrode RE. The sensing current Isensor is generated at the first electrode WE at first, flows through the resistor Rwr and the resistor Rrc and then enters the third electrode CE, and copies an output current Io through the cascode current mirror of the first transistor M1, the second transistor M2, the third transistor M3, and the fourth transistor M4. A Rin1 is an equivalent input resistor viewed from a CE terminal of the third electrode (a drain of the third transistor M3). The resistance of Rin1 is as shown in the first equation, that is, about mega ohms. Therefore, the resistor has very large input impedance, and is not suitable for serving as a current input terminal.

$$Rin1 \cong g_{m3} r_{o3} r_{o1} \qquad (I)$$

$$A_1 \beta_1(s) \cong A_1(s) \cdot \frac{g_{m1}}{g_{m3}} \cdot R_{sensor} \qquad (II)$$

The loop gain is as shown in the second equation: when Rsensor (that is, Rwr) changes, a maximum value of the loop gain is also influenced, which has a negative impact on the stability.

The signal readout circuit of the amperometric sensor shown in FIG. 2 has advantages such as low power and a small chip area. However, as the equivalent input resistance (Rin1) of the readout circuit is too large, signal oscillation will occur when the sensing current is smaller than a microampere level.

SUMMARY OF THE INVENTION

In view of the above, the present invention provides a signal readout circuit of an amperometric sensor, which is adapted to solve problems and eliminates disadvantages of the prior art.

A signal readout circuit according to an embodiment of the present invention comprises a first amplifier, a second amplifier and first to fourth transistors. The signal readout circuit has a first electrode, a second electrode, and a third electrode. A voltage is input from a first input terminal of the first amplifier. A second input terminal of the first amplifier is electrically connected to the second electrode. A gate and a drain of the first transistor are connected to a first input terminal of the second amplifier. A source of the first transistor is connected to a ground terminal. A gate of the second transistor is electrically connected to the gate of the first transistor. A drain of the second transistor is electrically connected to a second input terminal of the second amplifier. A source of the second transistor is connected to a ground terminal. A gate of the third transistor is electrically connected to an output terminal of the first amplifier. A source of the third transistor is electrically connected to the third electrode. A drain of the third transistor is electrically connected to the drain of the first transistor. A gate of the fourth transistor is electrically connected to an output terminal of the second amplifier. A drain of the fourth transistor is connected to a load. A source of the fourth transistor is electrically connected to the drain of the second transistor. The voltage input from the first input terminal of the first amplifier is a fixed voltage.

The present invention discloses a signal readout circuit applied in a wide current-sensing range for chemical sensing based on amperometric detection. The readout circuit may be applied in electrochemical sensing of different compounds, such as glucose, lactate, ascorbic acid etc., so as to read out a current signal of an amperometric sensor. Through a design of low input impedance, sensing signals in a wide current range can be sensed in the present invention. Also, a current mirror structure is used to copy the input current to an output current, such that an output signal range of the output signals of the current circuit is not limited by a supplied voltage.

For purposes of summarizing, some aspects, advantages and features of some embodiments of the invention have been described in this summary. Not necessarily all of (or any of) these summarized aspects, advantages or features will be embodied in any particular embodiment of the invention. Some of these summarized aspects, advantages and features and other aspects, advantages and features may become more fully apparent from the following detailed description and the appended claims.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Certain embodiments of the invention relate generally to electronic dispersion compensation systems and methods. However, the disclosed embodiments of systems and methods may be used in other contexts unrelated to electronic dispersion compensation.

The detailed features and advantages of the present invention are described below in detail through the following embodiments. The content of the detailed description is sufficient for those skilled in the art to understand the technical content of the present invention and to implement the present invention accordingly. Based upon the content of the specification, claims, and drawings, those skilled in the art can easily understand the relevant objectives and advantages of the present invention. The following embodiments are intended to describe the present invention in further detail, but are not intended to limit the scope of the present invention in any way.

Figure 3:
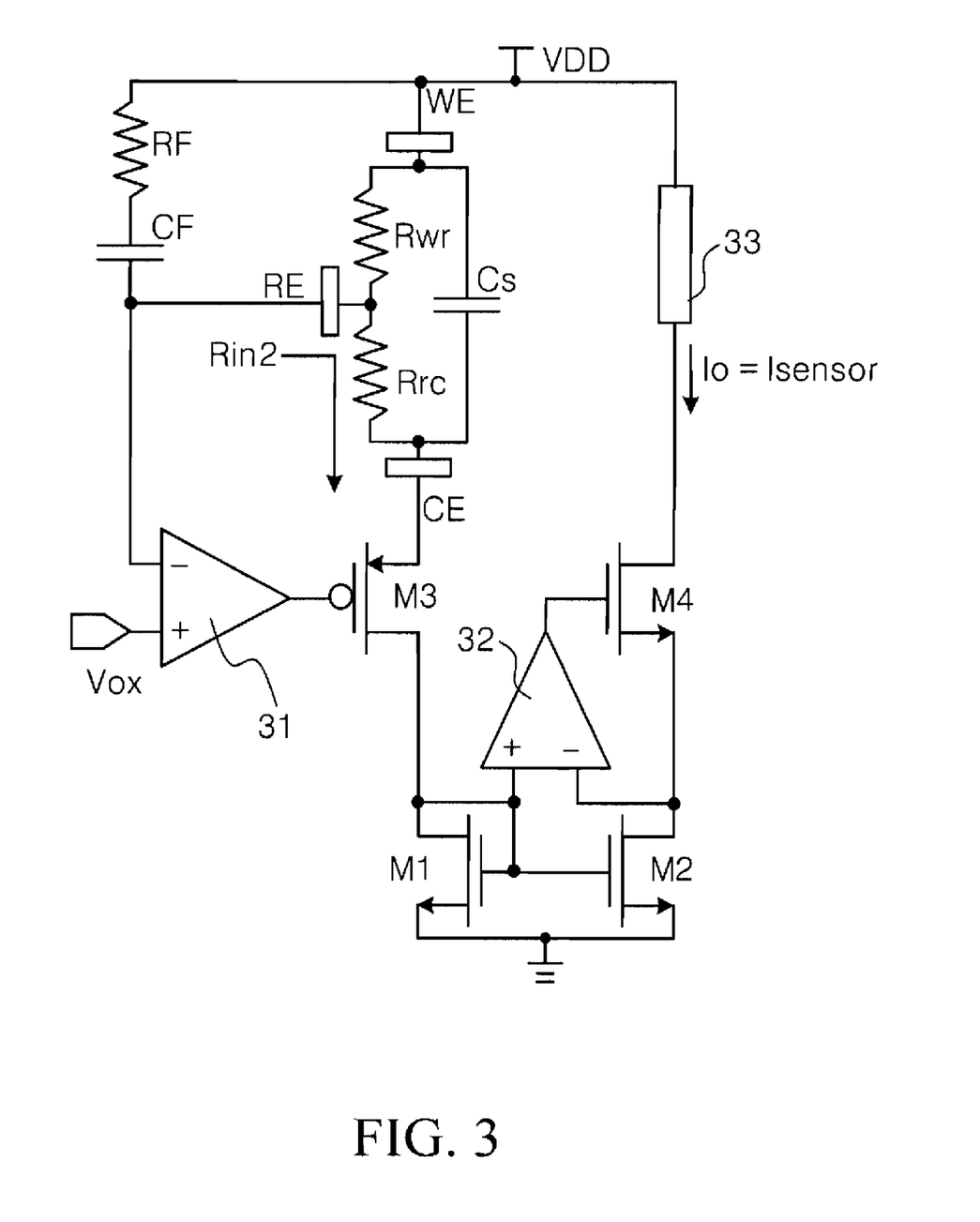
FIG. 3 is a schematic circuit diagram of a signal readout circuit of an amperometric sensor according to the present invention.

FIG. 3 is a schematic circuit diagram of a signal readout circuit of an amperometric sensor according to the present invention. The signal readout circuit comprises a first amplifier 31, a second amplifier 32, a first transistor M1, a second transistor M2, a third transistor M3, and a fourth transistor M4. A resistor Rwr, a resistor Rrc, and a capacitor Cs are equivalent resistors and capacitor of a glucose solution. The resistor Rwr is a Faraday resistor, and resistance of the resistor Rwr will decrease with the increase of a sensing current. The resistor Rrc is solution impedance. The capacitor Cs is an electric double layer capacitor of a working electrode. The resistor Rrc and the capacitor Cs will not change with currents. The signal readout circuit has a first electrode WE, a second electrode RE, and a third electrode CE.

The first amplifier 31 has a first input terminal, a second input terminal, and an output terminal. A voltage Vox is input from the first input terminal. The second terminal is electrically connected to the second electrode RE. The voltage Vox is an input pin for setting a potential of the second electrode RE. In an embodiment, the voltage Vox is a fixed voltage. The second amplifier 32 has a first input terminal, a second input terminal, and an output terminal. Here, the first input terminal is a positive input terminal, and the second input terminal is a negative input terminal. In an embodiment, the first amplifier is an operational transconductance amplifier (OTA). In another embodiment, the second amplifier is a self-biased differential amplifier.

The first transistor M1 has a gate, a drain, and a source. The gate and the drain of the first transistor M1 are connected to the first input terminal of the second amplifier 32. The source of the first transistor M1 is connected to a ground terminal. In this embodiment, the first transistor M1 is a diode-connected metal oxide semiconductor (MOS) transistor. In another embodiment, the first transistor M1 is an N-channel MOS (NMOS) transistor.

The second transistor M2 has a gate, a drain, and a source. The gate of the second transistor M2 is electrically connected to the gate of the first transistor M1. The drain of the second transistor M2 is electrically connected to the second input terminal of the second amplifier 32. The source of the second transistor M2 is connected to the ground terminal. In this embodiment, the second transistor M2 is an NMOS transistor.

The third transistor M3 has a gate, a drain, and a source. The gate of the third transistor M3 is electrically connected to the output terminal of the first amplifier 31. The source is electrically connected to the third electrode CE. The drain of the third transistor M3 is electrically connected to the gate of the first transistor M1. In this embodiment, the third transistor M3 is a P-channel MOS (PMOS) transistor.

The fourth transistor M4 has a gate, a drain, and a source. The gate of the fourth transistor M4 is electrically connected to the output terminal of the second amplifier 32. The drain of the fourth transistor M4 is connected to a load 33. The source of the fourth transistor M4 is electrically connected to the drain of the second transistor M2. Another terminal of the load 33 is also connected to the first electrode WE. In this embodiment, the fourth transistor M4 is an NMOS transistor.

Rin2 is an equivalent input resistor viewed from a terminal of the third electrode CE (the drain of the third transistor M3), and the resistance of Rin2 is as shown in the third equation.

$$R_{in2} \cong \frac{\frac{1}{g_{m1}} + r_{o3}}{1 + g_{m3} \cdot r_{o3}} \cong \frac{1}{g_{m3}} \quad \text{(III)}$$

Thus, as can be seen from the third equation, the equivalent input resistor Rin2 is reduced significantly in comparison with the circuit of FIG. 2.

In another embodiment, the readout circuit further comprises a frequency compensation circuit, which is formed by a resistor RF and a capacitor CF. The objective of the frequency compensation circuit is to add a zero point to an internal dominant pole of the OTA, so as to expand a phase margin.

In another embodiment, the second amplifier 32 is a self-biased differential amplifier, so as to improve a current matching degree of the first transistor M1 and the second transistor M2. In addition, the fourth transistor M4 may also be biased, and no additional bias voltage is needed. As shown in FIG. 2, an additional bias voltage Vbias is needed.

For the loop gain part, the analysis is as shown in the fourth equation:

$$A_2\beta_2(s) \cong A_2(s) \cdot \frac{R_{sensor}}{\frac{1}{g_{m3}} + R_{sensor}}, \frac{1}{g_{m3}} << R_{sensor} \quad (IV)$$

When the resistor Rwr is changed, a maximum value of the loop gain is not influenced, and stability does not change easily.

Performance comparison between the signal readout circuit of the present invention and the signal readout circuit in FIG. 2 is illustrated in the following.

The process used in the circuit simulation is TSMC 0.35 μm mixed-signal 2P4M 3.3V CMOS models, and HSpice software is used for simulation. The oxidation potential for the glucose sensing for this simulation is 0.4 V (an oxidation potential of an electrode used in this experiment). This voltage is found by using cyclic voltammetry. The tested electrode is an Abbe's three-electrode test piece. Therefore, it is set that the Vox voltages in FIGS. 2 and 3 are 2.9 V (3.3 V−0.4 V=2.9 V). The Rwr is modulated to simulate the generation of a limited current for stable mass transfer. In FIGS. 2 and 3, a load element is temporarily replaced by a resistor. In actual applications, the load is a current-type analog-to-digital converter. The following simulation results are all obtained through post-simulation. For ease of comparison, the circuit in FIG. 2 is referred to as Readout-1, and the circuit in FIG. 3 is referred to as Readout-2.

Comparison of the loop gain and phase margin is illustrated first.

Figure 4:
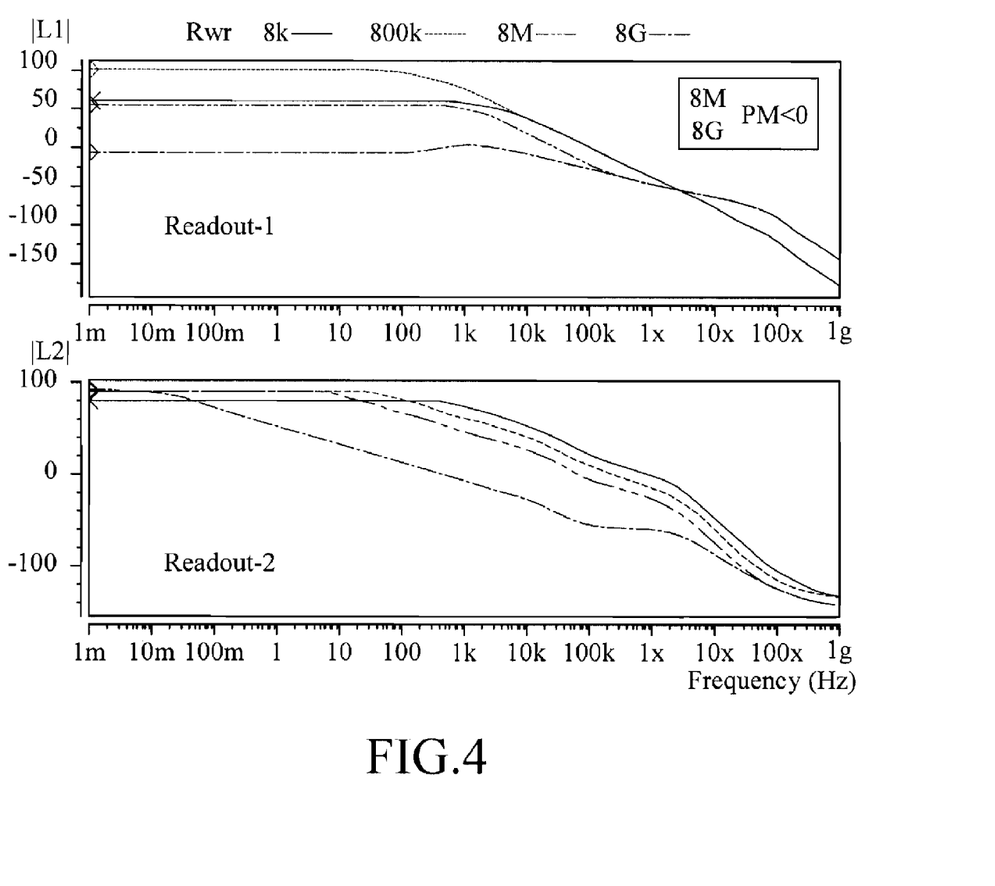
FIG. 4 shows a simulation result of loop gains of the signal readout circuits in FIGS. 2 and 3.

The Rwr simulates the sensing currents of 50 μA, 0.5 μA, 50 nA, and 50 pA with 8 kΩ, 800 kΩ, 8 MΩ, and 8 GΩ respectively. FIG. 4 shows a simulation result of loop gains of Readout-1 and Readout-2. In the Readout-1 part, the simulation result complies with the third equation when the Rwr is equal to 8 kΩ and 800 kΩ. When the Rsensor (Rwr) is greater, the maximum value of the loop gain will be greater, but the phase margin will be smaller. When the Rwr is equal to 8 MΩ and 8 GΩ, the phase margin is smaller than zero (PM<0), and the circuit is unstable.

In the Readout-2 part, the simulation result is as analyzed in the fourth equation. The maximum value of the loop gain is not sensible to the changes of the Rsensor (Rwr), and the phase margin is in a safe range.

Figure 5:
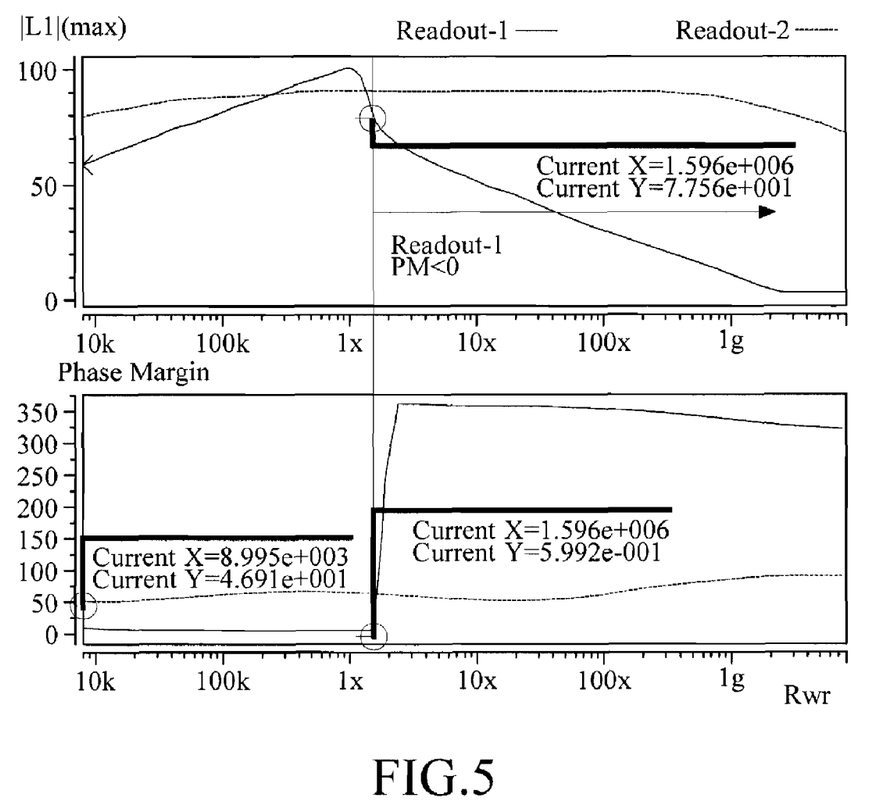
FIG. 5 shows a comparison between loop gains or phase margins of the signal readout circuits in FIGS. 2 and 3.

FIG. 5 is a consecutive scanning of the Rwr from 8 kΩ to 8 GΩ. Ten points are scanned in each decade of frequency. The maximum value of the loop gain of the Readout-1 is in direct proportion to the Rwr when the Rwr is smaller than 1.6 MΩ (the sensing current is greater than 0.25 μA). However, when the Rwr is greater than 1.6 MΩ (the sensing current is smaller than 0.25 μA), the phase margin is already smaller than zero, which is the major reason that the lowest sensing current of the Readout-1 cannot be reduced. Only input currents at micro-levels can be sensed. In the Readout-2, the maximum value of the loop gain and the phase margin are irrelevant to the changes of the Rsensor (Rwr), presenting a stable characteristic curve.

Figure 6:
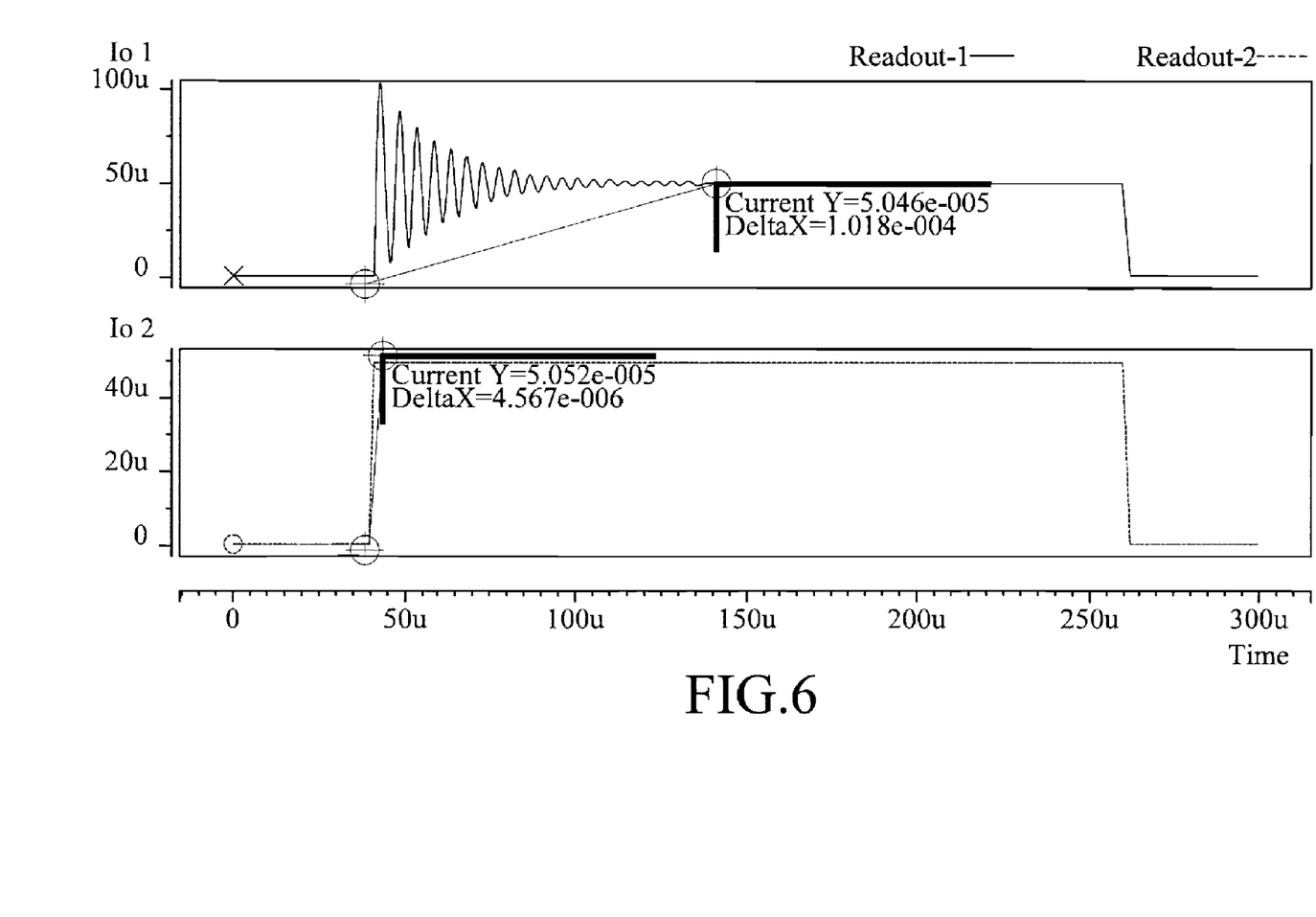
FIG. 6 shows a transient analysis comparison between signal readout circuits in FIGS. 2 and 3.

FIG. 6 shows a transient analysis comparison. As can be seen from FIG. 6, the newly proposed Readout-2 greatly solves the oscillation problem of the Readout-1. The input current is a 50 μA square wave current. The range of the square wave is from 40 μs to 260 μs. The settling time of the Readout-1 is 101.8 μs. The settling time of the Readout-2 is 4.57 μs. Therefore, the settling time is shortened substantially.

Figure 7:
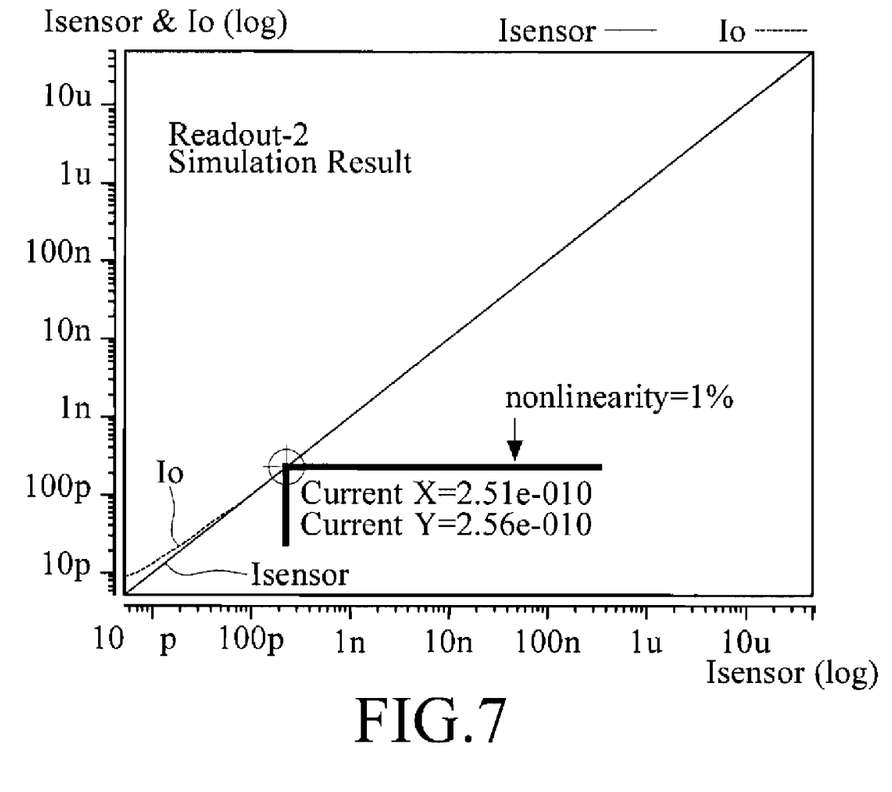
FIG. 7 shows a direct current analysis of the signal readout circuit of an amperometric sensor according to the present invention.

FIG. 7 shows a direct current analysis of the readout circuit according to the present invention. A characteristic curve on which the output current (Io) of the readout circuit is corresponding to the sensing current (Isensor) is illustrated. The ordinates and abscissas are log coordinates, and the minimum value of the sensing current is 250 pA when non-linearity of the output current to the input current is 1%.

Figure 8:
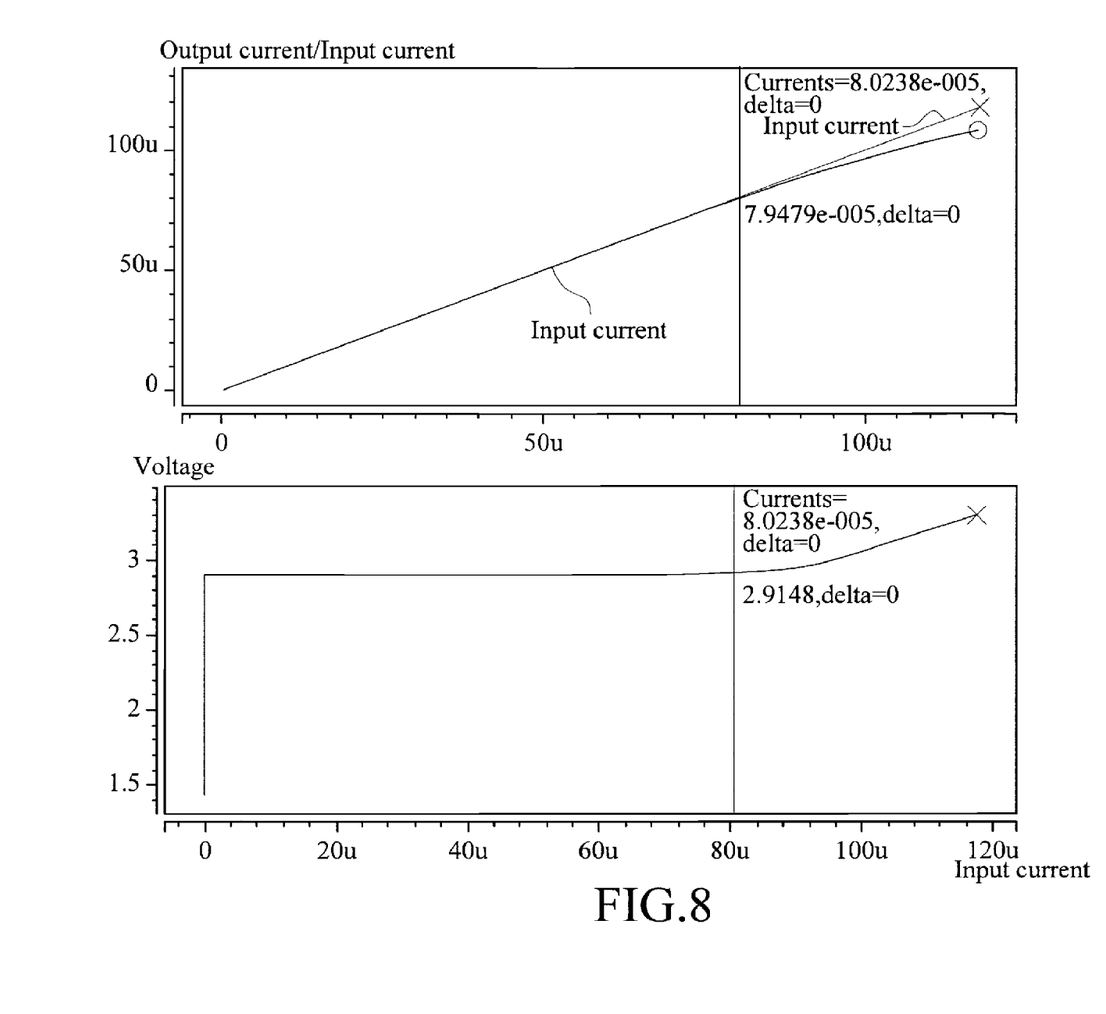
FIG. 8 shows a sensing current range of the signal readout circuit of an amperometric sensor according to the present invention.

FIG. 8 shows that the maximum value of the sensing current is 80 μA when the non-linearity of the output current to the input current is 1%. Thus, the sensing current range of the readout circuit according to the present invention is 250 pA to 80 μA.

The simulation results are arranged and compared in the following table. It may be clearly seen that the sensing current range and the settling time of the Readout-2 are obviously better than those of the Readout-1.

| Characteristics | Readout-1 | Readout-2 |
|---|---|---|
| Sensing range | 1 μA to 50 μA ($10^1$) | 250 pA to 50 μA ($10^5$) |
| Power consumption (Isensor at 250 pA to 50 μA) | 390 μW to 720 μW | 390 μW to 745 μW |
| Input impedance (open loop) | 924 MΩ | 31.6 kΩ |
| Phase margin (worst case) | PM < 0 when Isensor at nA range | 47° when Isensor = 50 μA |
| Whether the loop gain is influenced by the impedance of the sensor | Yes | No |
| Signal oscillation | Yes | No |
| settling time (at 1%) | 101.8 μs | 4.57 μs |
| Chip area | 0.16 mm$^2$ | 0.176 mm$^2$ |

The present invention discloses a signal readout circuit applied in a wide current-sensing range of amperometric chemical sensing. The readout circuit may be applied in electrochemical sensing such as glucose, so as to read out a current signal of the amperometric sensor. Through a design of low input impedance, the present invention can sense sensing signals in a wide current range. Also, a current mirror structure is used to copy the input current into an output current, such that a range of output signals of the amperometric circuit is not limited by the supply voltage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A signal readout circuit of an amperometric sensor, comprising:
   a first electrode, a second electrode, a third electrode;

a first amplifier, having a first input terminal, a second input terminal, and an output terminal, wherein a voltage is input from the first input terminal, and the second input terminal is electrically connected to the second electrode;
a second amplifier, having a first input terminal, a second input terminal, and an output terminal;
a first transistor, having a gate, a drain, and a source, wherein the gate and the drain are connected to the first input terminal of the second amplifier, and the source is connected to a ground terminal;
a second transistor, having a gate, a drain, and a source, wherein the gate is electrically connected to the gate of the first transistor, the drain is electrically connected to the second input terminal of the second amplifier, and the source is connected to the ground terminal;
a third transistor, having a gate, a drain, and a source, wherein the gate is electrically connected to the output terminal of the first amplifier, the source is electrically connected to the third electrode, and the drain is electrically connected to the drain of the first transistor; and
a fourth transistor, having a gate, a drain, and a source, wherein the gate is electrically connected to the output terminal of the second amplifier, the drain is connected to a load, and the source is electrically connected to the drain of the second transistor.

2. The circuit according to claim 1, wherein the voltage input from the first input terminal of the first amplifier is a fixed voltage.

3. The circuit according to claim 1, further comprising a frequency compensation unit.

4. The circuit according to claim 3, wherein the frequency compensation unit comprises a resistor and a capacitor connected to the resistor.

5. The circuit according to claim 1, wherein the first transistor is a diode-connected metal-oxide semiconductor (MOS).

6. The circuit according to claim 1, wherein the first transistor is an N-channel MOS (NMOS) transistor.

7. The circuit according to claim 1, wherein the second transistor is an NMOS transistor.

8. The circuit according to claim 1, wherein the third transistor is a P-channel MOS (PMOS) transistor.

9. The circuit according to claim 1, wherein the fourth transistor is an NMOS transistor.

10. The circuit according to claim 1, wherein the first amplifier is an operational transconductance amplifier.

11. The circuit according to claim 1, wherein the second amplifier is a self-biased differential amplifier.

* * * * *